(12) United States Patent
Okada et al.

(10) Patent No.: US 10,456,200 B2
(45) Date of Patent: Oct. 29, 2019

(54) CATHETER, EXAMINATION SYSTEM AND THROMBUS REMOVING DEVICE

(75) Inventors: Hiroyuki Okada, Shizuoka (JP); Teiji Nakayama, Shizuoka (JP); Kazuo Umemura, Shizuoka (JP); Daisuke Yamashita, Shizuoka (JP); Yutaka Yamashita, Shizuoka (JP); Katsuhiro Kobayashi, Shizuoka (JP)

(73) Assignees: Teiji Nakayama, Hamamatsu-shi, Shizuoko (JP); HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 1004 days.

(21) Appl. No.: 12/091,075

(22) PCT Filed: Oct. 25, 2006

(86) PCT No.: PCT/JP2006/321224
§ 371 (c)(1),
(2), (4) Date: Apr. 22, 2008

(87) PCT Pub. No.: WO2007/049632
PCT Pub. Date: May 3, 2007

(65) Prior Publication Data
US 2009/0270846 A1 Oct. 29, 2009

(30) Foreign Application Priority Data
Oct. 25, 2005 (JP) ................................ P2005-310218

(51) Int. Cl.
*A61B 18/24* (2006.01)
*A61M 5/00* (2006.01)
(Continued)

(52) U.S. Cl.
CPC .............. *A61B 18/24* (2013.01); *A61B 90/39* (2016.02); *A61M 5/007* (2013.01); *A61M 2025/0037* (2013.01)

(58) Field of Classification Search
CPC .. A61N 1/3906; A61N 1/3912; A61N 1/3937; A61N 1/3956; A61N 1/3943
(Continued)

(56) References Cited

U.S. PATENT DOCUMENTS 4,784,144 A * 11/1988 Ono .................... A61B 1/00165
385/117
4,785,806 A * 11/1988 Deckelbaum ..................... 606/7
(Continued)

FOREIGN PATENT DOCUMENTS

EP 0 355 996 A2 2/1990
JP 60-263109 12/1985
(Continued)

OTHER PUBLICATIONS

A reconstituted in vitro clot model for evaluating laser thrombolysis. Janis AD1, Buckley LA, Nyara AN, Prahl SA, Gregory K.J Thromb Thrombolysis. Jun. 2002;13(3):167-75.*

*Primary Examiner* — Wade Miles
*Assistant Examiner* — Matthew P Saunders
(74) *Attorney, Agent, or Firm* — Drinker Biddle & Reath LLP

(57) ABSTRACT

The position of a metal marker 5 relative to an optical fiber 6 is fixed, and the metal marker 5 can be moved up close to a target site such as a thrombus. It is preferable that the position, in an optical fiber longitudinal direction, of a front-end face of the optical fiber 6 is coincident with the position, in an optical fiber longitudinal direction, of a front-end face of the metal marker 5. More specifically, since the distance between the target site and the front end of the
(Continued)

optical fiber 6 is known by radiography, it becomes unnecessary to use a large quantity of contrast agent and irradiate a laser beam depending on skill and intuition, and therefore an effective laser beam irradiation becomes possible.

5 Claims, 3 Drawing Sheets

(51) Int. Cl.
    *A61M 25/00*     (2006.01)
    *A61B 90/00*     (2016.01)

(58) Field of Classification Search
    USPC ....... 607/1, 2, 7, 13–16, 88, 89; 606/1, 2, 7, 606/13–16
    See application file for complete search history.

(56) References Cited

U.S. PATENT DOCUMENTS

| | | | |
|---|---|---|---|
| 5,005,180 A * | 4/1991 | Edelman et al. | ................ 372/57 |
| 5,034,010 A | 7/1991 | Kittrell et al. | |
| 5,053,006 A * | 10/1991 | Watson | ................ 604/20 |
| 5,053,033 A * | 10/1991 | Clarke | ................ A61N 5/0601 606/15 |
| 5,199,431 A * | 4/1993 | Kittrell et al. | ................ 600/477 |
| 5,344,419 A | 9/1994 | Spears | |
| 5,383,467 A * | 1/1995 | Auer et al. | ................ 600/342 |
| 5,466,234 A * | 11/1995 | Loeb et al. | ................ 606/15 |
| 5,496,305 A * | 3/1996 | Kittrell et al. | ................ 606/15 |
| 5,540,677 A * | 7/1996 | Sinofsky | ................ A61B 18/22 606/10 |
| 5,573,531 A * | 11/1996 | Gregory | ................ 606/14 |
| 5,693,043 A * | 12/1997 | Kittrell et al. | ................ 606/15 |
| 5,817,144 A * | 10/1998 | Gregory | ................ 607/89 |
| 5,944,687 A * | 8/1999 | Benett et al. | ................ 604/22 |
| 5,989,243 A | 11/1999 | Goldenberg | |
| 6,022,309 A * | 2/2000 | Celliers et al. | ................ 600/7 |
| 7,740,626 B2 * | 6/2010 | Takayama | ................ A61B 18/26 606/15 |
| 8,900,219 B2 * | 12/2014 | Sinofsky | ................ A61B 5/7264 606/2 |
| 2003/0165313 A1* | 9/2003 | Broeng | ................ G02B 6/02357 385/125 |
| 2004/0006333 A1 | 1/2004 | Arnold et al. | |
| 2005/0014995 A1* | 1/2005 | Amundson | ................ A61B 1/018 600/105 |
| 2005/0131400 A1* | 6/2005 | Hennings et al. | ................ 606/15 |
| 2005/0192480 A1* | 9/2005 | Toriya | ................ A61B 1/00167 600/182 |
| 2005/0272975 A1* | 12/2005 | McWeeney | ................ A61B 1/00071 600/113 |
| 2006/0013544 A1* | 1/2006 | Bouma | ................ G02B 6/02042 385/116 |
| 2009/0299354 A1* | 12/2009 | Melsky | ................ A61B 18/245 606/16 |

FOREIGN PATENT DOCUMENTS

| | | |
|---|---|---|
| JP | 7-255737 | 10/1995 |
| JP | 2000-508938 | 7/2000 |
| JP | 3222885 | 8/2001 |
| WO | WO-02/26150 A1 | 4/2002 |

\* cited by examiner

CATHETER, EXAMINATION SYSTEM AND THROMBUS REMOVING DEVICE

TECHNICAL FIELD

The present invention relates to a catheter, an examination system, and a thrombus removing device.

BACKGROUND ART

A catheter is a flexible tube with a diameter of approximately 2 mm and a length of approximately 1 m. The catheter can be inserted from a femoral artery and advanced to a target site such as the heart or the brain. When a contrast agent is supplied from the front end of the catheter, radiography can be performed.

A catheter through a hole of which a guide wire is passed has been known. When the catheter is inserted from a femoral region, first, the wire is first inserted in the femoral region, and then the catheter is sent out along the guide wire, whereby the catheter can be made to reach a target site.

For a thrombolytic treatment of heart and brain vessels, a catheter is inserted in the body, and a thrombolytic agent (urokinase) is released from a front-end portion thereof. Moreover, a thrombolytic treatment using a laser beam is also known. Since the laser beam is attenuated by blood vessels, several devices have been proposed.

In a thrombolytic treatment described in the following Patent Document 1, it has been described that attenuation of a laser beam can be suppressed by advancing a laser beam into a contrast agent while releasing the contrast agent from the front-end portion of a catheter, whereby a thrombus can be dissolved. It has been provided that the laser beam is emitted from a movable optical fiber through a hole provided in the catheter.

In a thrombolytic treatment described in the following Patent Document 2, it has been provided that a pulsed laser radiation is emitted from the front end of an optical fiber protruded from the front-end portion of a capillary tube to cause ultrasonic vibration, whereby a thrombus can be dissolved.

Patent Document 1: Japanese Patent Registration No. 322885

Patent Document 2: Japanese Translation of International Application (Kohyo) No. 2000-508938

DISCLOSURE OF THE INVENTION

Problem to be Solved by the Invention

Meanwhile, with a conventional catheter, since the distance between a laser beam and a thrombus is unclear, a large quantity of contrast agent has been used and a laser beam has been emitted depending on skill and intuition, and thus the laser beam could not be effectively irradiated onto a target such as a thrombus.

The present invention has been made in view of such a problem, and an object thereof is to provide a catheter which can effectively irradiate an object with a laser beam and an examination system and a thrombus removing device which can effectively dissolve a thrombus as the object.

Means for Solving the Problem

In order to solve the problem described above, a catheter according to the present invention includes: a resinous capillary tube having a hole to pass a wire therethrough; a marker attached to a front-end portion of the capillary tube; and an optical fiber which is buried in the capillary tube and whose position relative to the marker is fixed, wherein a position, in an optical fiber longitudinal direction, of a front-end face of the optical fiber is coincident with a position, in an optical fiber longitudinal direction, of a front-end face of the marker. The front end of the optical fiber can be approximated to such an extent as to contact a thrombus or up to a close range. In such a state, it becomes possible to dissolve a thrombus more safely by only irradiating a laser beam with a specific wavelength, a specific pulse width, and a repetition frequency from the optical fiber.

When the catheter is inserted from a femoral region, the wire is first inserted in the femoral region, and then the catheter is sent out along the wire, whereby the catheter is made to reach a target site. In this case, when radiography is performed, the marker is displayed on a screen. As the marker, a metal marker that absorbs X-rays is favorably used. Since the position of this metal marker relative to the optical fiber is fixed, the metal marker can be moved up close to the target site such as a thrombus. More specifically, since the distance between the target site and the front end of the optical fiber is known, it becomes unnecessary to use a large quantity of contrast agent and irradiate a laser beam depending on skill and intuition, and therefore an effective laser beam irradiation becomes possible.

It is preferable that the catheter further includes a resin material interposed between the optical fiber and the capillary tube. The resin material is also bent when the catheter is curved, to suppress trace elements in blood from entering. Therefore, deterioration of the optical fiber can be prevented.

An examination system having this catheter includes: the catheter; and a light source which emits light to be inputted to the optical fiber of the catheter. Here, it is preferable the light source is a laser light source, and a center wavelength $\lambda$, a pulse width T, and a repetition frequency f of the laser beam are set as follows:

$520 \text{ nm} \leq \lambda \leq 590 \text{ nm}$ $1 \text{ } \mu\text{sec} \leq T \leq 100 \text{ } \mu\text{sec}$ $1 \text{ Hz} \leq f \leq 10 \text{ Hz}$ In this case, since the laser beam effectively acts for thrombolysis and does not act on vessel walls, a thrombus can be dissolved efficiently and safely in a short time.

Effects of the Invention

According to the catheter, examination system, and thrombus removing device of the present invention, a laser beam can be effectively irradiated onto a target, so that a thrombus being the target can be effectively dissolved.

DESCRIPTION OF SYMBOLS

1 . . . catheter, 2 . . . wire, 3 . . . hole, 5 . . . marker, 6 . . . optical fiber, 7 . . . branching adapter, 8 . . . connector, 9 . . . contrast agent introducing tube, 10 . . . connector, 11 . . . packing, 12 . . . terminal cap, 13 . . . connector, 61a . . . ferule, 61 . . . optical fiber, DRV . . . drive circuit, DSP . . . display, INJ . . . contrast agent injector, LD . . . laser diode.

BEST MODES FOR CARRYING OUT THE INVENTION

Hereinafter, a catheter, an examination system, and a removing device according to an embodiment will be described. Here, identical elements are designated with identical numerical symbols so as to avoid overlapping descriptions.

Figure 1:
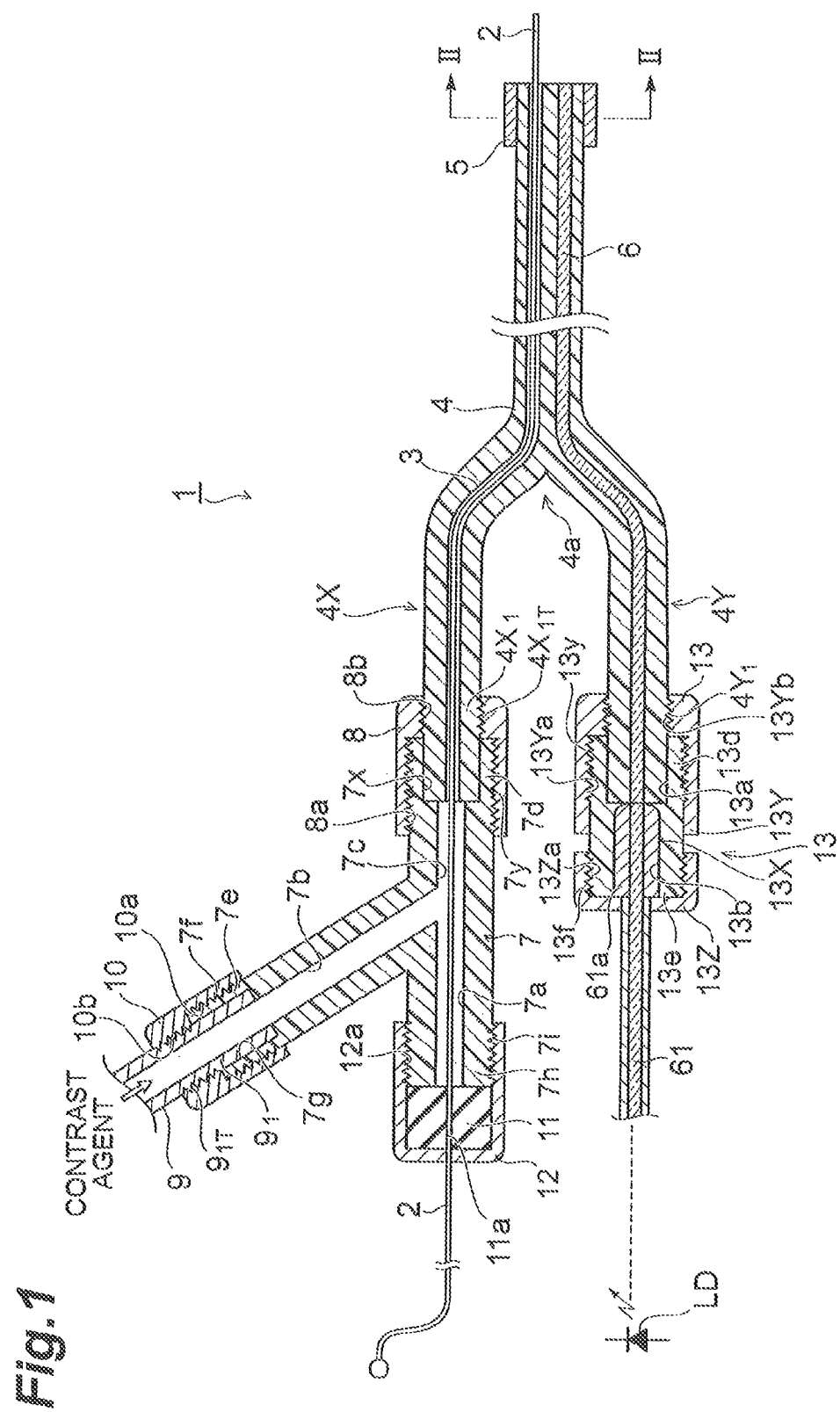
FIG. 1 A longitudinal sectional view of a catheter.

FIG. 1 is a longitudinal sectional view of a catheter.

A catheter 1 includes a resinous capillary tube 4 having a hole 3 to pass a wire 2 therethrough, a metal marker 5 attached to a front-end portion of the capillary tube 4, and an optical fiber 6 which is embedded in the capillary tube 4 and whose position relative to the metal marker 5 is fixed.

The capillary tube 4 has a branching portion 4a, and the hole 3 passes through one branched capillary tube 4X and an optical fiber 6 passes through the other branched capillary tube 4Y. The annular metal marker 5 made of a metal such as platinum is fitted to the front-end portion of the capillary tube 4, and is thus fixed to the capillary tube 4. The metal marker 5 may be formed by plating or vapor-depositing the resin capillary tube 4 with a metal material.

To a base-end portion of the branched capillary tube 4X, a Y-type branching adapter 7 is fixed. The branching adapter 7 has a wire inserting through-hole 7a and a contrast agent introducing through-hole 7b, these through-holes 7a and 7b are connected at the branching capillary tube 4X side to form a common through-hole 7c, and this is connected with the hole 3 of the branched capillary tube 4X. The branched capillary tube 4X and the branching adapter 7 are coupled by a connector 8.

A coupling portion 7d at the branched capillary tube 4X side of the branching adapter 7 has a screw portion 7y at the periphery and includes, at the inside, a branched capillary tube insertion hole 7x communicated with the common through-hole 7c. A base-end portion 4X1 of the branched capillary tube 4X is inserted in the branched capillary tube insertion hole 7x, and the periphery of the base-end portion 4X1 has a screw portion 4X1T.

The connector 8 forms a cap being a cylinder with a bottom, has a screw portion 8a at the inner surface of its cylindrical portion, and has a screw portion 8b at the inside of an opening of its bottom portion. When the connector 8 serving as a cap is screwed on, the screw portions 8a and 8b at the inside thereof are screwed with screw portions 7y and 4X1T formed on the periphery of the coupling portion 7d and the periphery of the base-end portion 4X1, whereby the branching adapter 7 is fixed to the branched capillary tube 4X.

A connecting portion 7e at the side of a contrast agent introducing tube 9 of the branching adapter 7 has a screw portion 7f at the periphery and includes, at the inside, a contrast agent introducing tube insertion hole 7g communicated with the contrast agent introducing through-hole 7b. In the contrast agent introducing tube insertion hole 7g, a base-end portion 91 of the contrast agent introducing tube 9 is inserted, and the periphery of the base-end portion 91 has a screw portion 91T.

The connector 10 forms a cap being a cylinder with a bottom, has a screw portion 10a at the inner surface of its cylindrical portion, and has a screw portion 10b at the inside of an opening at its bottom portion. When the connector 12 serving as a cap is screwed on, the screw portions 10a and 10b at the inside thereof are screwed with the screw portions 7f and 91T formed on the periphery of the coupling portion 7e and the periphery of the base-end portion 91, whereby the contrast agent introducing tube 9 is fixed to the branching adapter 7.

A wire inserting tail-end portion 7h of the branching adaptor 7 has a screw portion 7i at the periphery and includes, on its tail-end face, a packing 11 that blocks the wire inserting through-hole 7a.

A tail-end cap 12 is a cylinder with a bottom, and has a screw portion 12a at the inner surface of its cylinder portion. When the cap 12 is screwed on, the screw portion 12a at the inside thereof is screwed with the screw portion 7i formed on the periphery of the wire inserting tail-end portion 7h, and the packing 11 is pressed against the wire inserting tail-end portion 7h. The columnar-shaped packing 11 has a wire passing hole 11a at the center, and the wire 2 passes through the wire passing hole 11a.

To a base-end portion of the branched capillary tube 4Y, another optical fiber 61 is connected via a connector 13, and the optical fiber 61 within the branched capillary tube 4Y is optically coupled with the optical fiber 61. A ferrule 61a is attached to the periphery of the optical fiber 61. The connector 13 is composed of a connector body 13X and caps 13Y and 13Z provided at both ends of the connector body 13X. The connector body 13X has a branched capillary tube insertion hole 13a and a ferule insertion hole 13b, and these insertion holes 13a and 13b are communicated within the connector.

A coupling portion 13d at the branched capillary tube 4Y side of the connector body 13X has a screw portion 13y at the periphery. In the branched capillary tube insertion hole 13a, a base-end portion 4Y1 of the branched capillary tube 4Y is inserted, and the periphery of the base-end portion 4Y1 has a screw portion 4Y1T.

A cap 13Y forms a cylinder with a bottom, has a screw portion 13Ya at the inner surface of its cylindrical portion, and has a screw portion 13Yb at the inside of its bottom portion. When the cap 13Y is screwed on, the screw portions 13Ya and 13Yb at the inside thereof are screwed with screw portions 13y and 4Y1T formed on the periphery of the coupling portion 13d and the periphery of the base-end portion 4Y1, whereby the branched capillary tube 4Y is connected to the connector 13.

A coupling portion 13e at the ferule side of the connector body 13X has a screw portion 13f at the periphery. In the ferule insertion hole 13b, the ferule 61a that includes the optical fiber 61 is inserted. A cap 13Z forms a cylinder with a bottom, and has a screw portion 13Za at the inner surface of its cylindrical portion. When the cap 13Z is screwed on, the screw portion 13Za at the inside thereof is screwed with the screw portion 13f formed at the periphery of the coupling portion 13e, whereby the ferule 61a is fixed to the connector 13. Therefore, the ferule 61a and the branched capillary tube 4Y are coupled by the connector 13, and the optical fiber 61 and the optical fiber 6 within these respective portions are optically coupled.

Since a laser beam is introduced into the optical fiber 61 from a laser diode LD (light source), the laser beam is inputted to the optical fiber 6, and is emitted from the front end of the catheter 1.

When the catheter 1 is inserted in the body from a femoral region, the wire 2 that slides within the capillary tube 4 is first inserted in the femoral region, and then the catheter 1 is sent out along the wire, whereby the catheter 1 is made to reach a target site. In this case, when radiography of a front-end portion of the catheter is performed, the metal marker 5 is displayed on a screen of an X-ray apparatus.

The position of the metal marker 5 relative to the optical fiber 6 is fixed, and the metal marker 5 can be moved up close to the target site such as a thrombus. Although it is preferable that the position, in an optical fiber longitudinal direction, of a front-end face of the optical fiber 6 is coincident with the position, in an optical fiber longitudinal direction, of a front-end face of the metal marker 5, the invention is not limited thereto. More specifically, since the distance between the target site and the front end of the optical fiber 6 is known by radiography, it becomes unnecessary to use a large quantity of contrast agent and irradiate a laser beam depending on skill and intuition, and therefore an effective laser beam irradiation becomes possible.

In other words, the front end of the optical fiber 6 can be approximated to such an extent as to contact the thrombus or up to a close range. In such a state, it becomes possible to dissolve the thrombus more safely by only irradiating a laser beam with a specific wavelength, a specific pulse width, and a repetition frequency from the optical fiber 6.

Moreover, when radiography of the target site is performed, a contrast agent (iodine containing water-soluble contrast medium) is introduced via the contrast agent introducing tube 9 according to necessity, passed through the through-holes 7b, 7c, and 3, and released from the front end of the catheter 1. Also, when the contrast agent is introduced, it is preferable to withdraw the wire 2 from the capillary tube 4 of the catheter 1.

Figure 2:
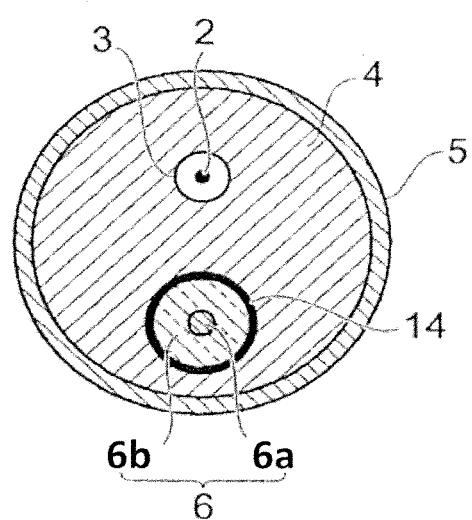
FIG. 2 A sectional view along arrows II-II of the catheter shown in FIG. 1.

FIG. 2 is a sectional view along arrows II-II of the catheter shown in FIG. 1.

The optical fiber 6 is provided in a buried condition in the resinous capillary tube (body) 4, and its longitudinal direction is coincident with a longitudinal direction of the capillary tube 4. The center position of the optical fiber 6 is off the center position in a section vertical to the longitudinal direction of the capillary tube 4, and the wire 2 passes through the inside of the hole 3 provided side by side with the optical fiber 6. The capillary tube 4 is made of a material such as Teflon (registered trademark).

A resin material 14 is interposed between the optical fiber 6 and the capillary tube 4. The resin material 14 is also bent when the catheter 1 is curved, to suppress trace elements in blood from entering the optical fiber 6, so that deterioration of the optical fiber 6 can be prevented. The resin material 14 is an elastic material, which is formed of a silicone resin or the like. Here, without using the resin material 14, the optical fiber 6 may be directly buried in the capillary tube 4.

As a method for burying the optical fiber 6, a method can be mentioned, which is for forming a capillary tube 4 opened with one hole by metallic molding, then passing an optical fiber 6 coated with an unsolidified resin material 14 through one narrow hole, and cutting a front-end portion of the capillary tube 4 along with the optical fiber 6 after the resin material 14 is solidified. Mechanical polishing is performed for this front-end portion.

Moreover, as another method, a method can be mentioned, which is for arranging an optical fiber 6 coated with a solidified resin material 14 and a molding wire such as a piano wire in a die for a capillary tube 4, introducing a capillary tube forming material into this die and solidifying the material, then withdrawing the molding wire from the capillary tube 4, and then cutting a front-end portion of the capillary tube 4 along with the optical fiber 6. Mechanical polishing is performed for this front-end portion.

Further, as a method for branching the capillary tube 4, a method for tearing one capillary tube up to halfway can be mentioned, besides the abovementioned metallic molding.

The optical fiber 6 is composed of a core 6a made of silica glass and a clad 6b located around the core 6a. A laser beam that has passed through the core 6a of the optical fiber 6 is emitted from the front-end face.

Figure 3:
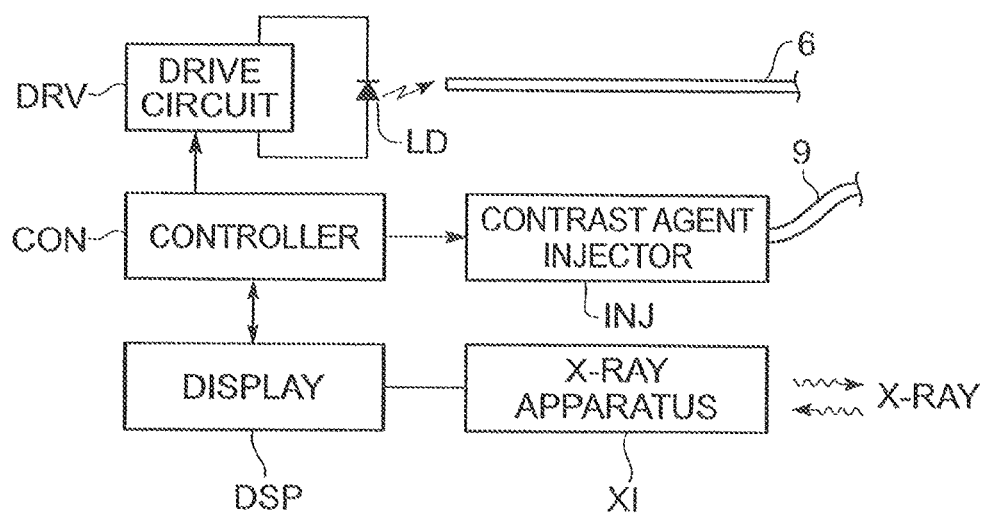
FIG. 3 block diagram of an inspection system to which the catheter shown in FIG. 1 is connected.

FIG. 3 is a block diagram of an inspection system to which the catheter shown in FIG. 1 is connected.

As described above, in this examination system, a thrombus can be dissolved more safely by only irradiating a laser beam with a specific wavelength, a specific pulse width, and a repetition frequency from the optical fiber 6. More specifically, the present examination system functions mainly as a thrombus removing device. The present examination system includes the catheter 1, the laser diode LD that emits a laser beam to be inputted to the optical fiber 6 of the catheter 1, and a drive circuit DRV of the laser diode LD.

A center wavelength $\lambda$, a pulse width T, and a repetition frequency f of the laser beam has the following relationship.

Center wavelength $\lambda$: 532 nm(effective wavelength: 520 nm$\leq\lambda\leq$590 nm)

1 $\mu$sec$\leq$T$\leq$100 $\mu$sec

1 Hz$\leq$f$\leq$10 Hz

In this case, since the laser beam effectively acts for thrombolysis and does not act on vessel walls, a thrombus can be dissolved efficiently and safely in a short time. The power of the laser beam is set to 10 to 100 mJ.

Laser driving conditions of the drive circuit DRV are set by a controller CON. After the catheter 1 is inserted in the body, the wire 2 is withdrawn, and a contrast agent is released from the contrast agent injector INJ into the contrast agent introducing tube 9 according to necessity. The contrast agent injector INJ is controlled by the controller CON.

When an image of the thrombus and marker 5 (see FIG. 5) is obtained by an X-ray apparatus XI, this image data is transferred to a display DSP of the controller CON and displayed on the display DSP. Once the thrombus and marker 5 approximate to visually contact each other on the screen, the controller CON inputs a control signal to the drive circuit DRV to drive the laser diode LD by the abovementioned conditions. This allows dissolving the thrombus very safely and efficiently.

Although, in the above embodiment, a laser light source (laser diode LD) has been exemplified as the light source, the light source is not limited thereto and may be, for example, a light-emitting diode, a DPSS laser (Diode Pumped Solid-State Laser) or the like.

INDUSTRIAL APPLICABILITY

The present invention can be used for a catheter, an examination system, and a thrombus removing device.

The invention claimed is:
1. An examination system comprising:
a catheter including:
a resinous capillary tube, comprising:
a trunk capillary tube comprised of resin, and having a front-portion that is surrounded by a marker made of platinum, and a branch portion that forms a first branched capillary tube comprised of resin and a second branched capillary tube comprised of resin, wherein the trunk capillary tube comprises a first through hole for at least one of a wire and a contrast agent, and a second through hole for an optical fiber, the wire passing through the first through hole, and the optical fiber passing through the second through hole;

a branching adapter fixed to the first branched capillary tube, and comprising resin and having a third branched capillary tube and a fourth branched capillary tube, wherein a through hole of the third branched capillary tube is continuous with the first through hole and comprises the wire, the fourth branched capillary tube comprising the contrast agent;

the optical fiber being fixed to the trunk capillary tube and in the second branched capillary tube, and having a position relative to the marker that is fixed in an optical fiber longitudinal direction; wherein a position, in the optical fiber longitudinal direction, of a front-end face of the optical fiber is coincident with a position, in the optical fiber longitudinal direction, of a front-end face of the marker;

a laser light source which emits light to be inputted to the optical fiber of the catheter, the light being emitted from the front-end face of the optical fiber comprising a pulsed laser beam;

a drive circuit of the laser light source; and a controller, and wherein laser driving conditions of the drive circuit are set by the controller, and the laser driving conditions of a center wavelength $\lambda$, a pulse width T, and a repetition frequency f of the pulsed laser beam are set as follows:

$520 \text{ nm} \leq \lambda \leq 590 \text{ nm}$, $1 \text{ μsec} \leq T \leq 100 \text{ μsec}$, and $1 \text{ Hz} \leq f < 10 \text{ Hz}$, a position of the optical fiber is shifted from the central axis of the second branched capillary tube to an off-center position at the branch portion of the trunk capillary tube; and a position of the first through hole is shifted from the central axis of the first branched capillary tube to an off-center position at the branch portion of the trunk capillary tube.

2. A thrombus removing device comprising:

a catheter including:
 a resinous capillary tube, comprising:
  a trunk capillary tube comprised of resin, and having a front-portion that is surrounded by a marker made of platinum, and a branch n portion that forms a first branched capillary tube comprised of resin and a second branched capillary tube comprised of resin, wherein the trunk capillary tube comprises a first through hole for at least one of a wire and a contrast agent, and a second through hole for an optical fiber, the wire passing through the first through hole, and the optical fiber passing through the second through hole;
 a branching adapter fixed to the first branched capillary tube, and comprising resin and having a third branched capillary tube and a fourth branched capillary tube, wherein a through hole of the third branched capillary tube is continuous with the first through hole and comprises the wire, the fourth branched capillary tube comprising the contrast agent;

the optical fiber being fixed to the trunk capillary tube and in the second branched capillary tube, and having a position relative to the marker that is fixed in an optical fiber longitudinal direction; wherein a position, in the optical fiber longitudinal direction, of a front-end face of the optical fiber is coincident with a position, in the optical fiber longitudinal direction, of a front-end face of the marker;

a laser light source which emits light to be inputted to the optical fiber of the catheter, the light being emitted from the front-end face of the optical fiber comprising a pulsed laser beam;

a drive circuit of the laser diode; and a controller, and wherein laser driving conditions of the drive circuit are set by the controller, and the laser driving conditions of a center wavelength $\lambda$, a pulse width T, and a repetition frequency f of the pulsed laser beam are set as follows:

$520 \text{ nm} \leq \lambda \leq 590 \text{ nm}$, $1 \text{ μsec} \leq T \leq 100 \text{ μsec}$, and $1 \text{ Hz} \leq f < 10 \text{ Hz}$, a position of the optical fiber is shifted from the central axis of the second branched capillary tube to an off-center portion at the branch of the trunk capillary tube; and;

a position of the first through hole is shifted from the central axis of the first branched capillary tube to an off-center position at the branch portion of the trunk capillary tube.

3. A thrombus removing device comprising:

a catheter including:
 a resinous capillary tube, comprising:
  a trunk capillary tube comprised of resin, and having front-portion that is surrounded by a marker made of platinum, and a branch portion that forms a first branched capillary tube comprised of resin and a second branched capillary tube comprised of resin, wherein the trunk capillary tube comprises a first through hole for at least one of a wire and a contrast agent, and a second through hole for an optical fiber, the wire passing through the first through hole, and the optical fiber passing through the second through hole;
 a branching adapter fixed to the first branched capillary tube, and comprising resin and having a third branched capillary tube and a fourth branched capillary tube, wherein a through hole of the third branched capillary tube is continuous with the first through hole and comprises the wire, the fourth branched capillary tube comprising the contrast agent;

the optical fiber being fixed to the trunk capillary tube and in the second branched capillary tube, and having a position relative to the marker that is fixed in an optical fiber longitudinal direction; wherein a laser light source which emits light to be inputted to the optical fiber of the catheter, the light being emitted from a front-end face of the optical fiber comprising a pulsed laser beam, a position of the optical fiber is shifted from the central axis of the second branched capillary tube to an off-center position at the branch portion of the trunk capillary tube; and a position of the first through hole is shifted from the central axis of the first branched capillary tube to an off-enter position at the branch portion of the trunk capillary tube.

4. A thrombus removing device according to claim 3, further comprising:
a drive circuit of the laser light source; and
a controller for the drive circuit.

5. A thrombus removing device according to claim 4, wherein the laser light source is a diode-pumped solid state laser.

* * * * *